United States Patent
Brown et al.

(10) Patent No.: US 10,434,234 B2
(45) Date of Patent: Oct. 8, 2019

(54) METHODS AND DEVICES FOR IDENTIFYING SUCTION EVENTS

(71) Applicant: HeartWare, Inc., Miami Lakes, FL (US)

(72) Inventors: Michael C. Brown, Boston, MA (US); Neil Voskoboynikov, Pembroke Pines, FL (US)

(73) Assignee: HeartWare, Inc., Miami Lakes, FL (US)

( * ) Notice: Subject to any disclaimer, the term of this patent is extended or adjusted under 35 U.S.C. 154(b) by 4 days.

(21) Appl. No.: 15/717,105

(22) Filed: Sep. 27, 2017

(65) Prior Publication Data
US 2018/0015213 A1 Jan. 18, 2018

Related U.S. Application Data

(62) Division of application No. 14/743,166, filed on Jun. 18, 2015, now Pat. No. 9,795,726.

(60) Provisional application No. 62/013,680, filed on Jun. 18, 2014.

(51) Int. Cl.
*A61M 1/10* (2006.01)
*A61M 1/12* (2006.01)

(52) U.S. Cl.
CPC ........ *A61M 1/1086* (2013.01); *A61M 1/1029* (2014.02); *A61M 1/122* (2014.02); *A61M 1/101* (2013.01); *A61M 2205/3334* (2013.01); *A61M 2205/3365* (2013.01); *A61M 2205/52* (2013.01)

(58) Field of Classification Search
CPC .............. A61M 1/1086; A61M 1/1029; A61M 2205/3334; A61M 2205/52; A61M 2205/3365

USPC .................................................... 607/15–17
See application file for complete search history.

(56) References Cited

U.S. PATENT DOCUMENTS

| | | | |
|---|---|---|---|
| 8,512,013 | B2 | 8/2013 | LaRose et al. |
| 2003/0045772 | A1 | 3/2003 | Reich et al. |
| 2003/0199727 | A1 | 10/2003 | Burke et al. |
| 2004/0152944 | A1 | 8/2004 | Medvedev et al. |
| 2004/0215050 | A1 | 10/2004 | Morello |
| 2012/0245681 | A1* | 9/2012 | Casas .................. A61M 1/1086 623/3.28 |

(Continued)

FOREIGN PATENT DOCUMENTS

WO 2003105669 A2 12/2003

OTHER PUBLICATIONS

Michael Vollkron, et al ., Development of a suction Detection System for Axial Blood Pumps, Artificial Organs 20 (8): 709-716, Blackwell Publishing, Inc.*

(Continued)

*Primary Examiner* — Catherine M Voorhees
*Assistant Examiner* — Roland Dinga
(74) *Attorney, Agent, or Firm* — Christopher & Weisberg, P.A.

(57) ABSTRACT

The present disclosure provides for a method, control device, and implantable system, for acquiring a plurality of flow rate data points over time, each data point indicative of a flow rate of blood through the pump, calculating, based on the plurality of acquired flow rate data points, a value characterizing one or more features of a waveform formed from the plurality of flow rate data points; and determining, based on the value, the presence or absence of a suction condition in the pump.

11 Claims, 9 Drawing Sheets

(56) References Cited

U.S. PATENT DOCUMENTS

2014/0100413 A1* 4/2014 Casas .................. A61M 1/1086
600/16

OTHER PUBLICATIONS

Michael Vollkron, et al., Development of a Suction Detection System for Axial Blood Pumps, Artificial Organs 28(8):709-716, Blackwell Publishing, Inc.
International Preliminary Report on Patentability, dated Oct. 10, 2016 for corresponding International Application No. PCT/US2015/036430; International Filing Date: Jun. 18, 2015 consisting of 17-pages.
International Search Report and Written Opinion for Application No. PCT/US2015/036430 dated Sep. 24, 2015.
Baloa, L.A. et al., "Cpntrol of Rotary Heart Assist Devices", American Control Conference, 2000. Proceedings of teh Jun. 28-30, 2000, Piscataway, NJ, USA, IEEE, vol. 5, Jun. 28, 2000 (Jun. 28, 2000), pp. 2982-2986.
China National Intellectual Property Administration, Notice on the First Office Action, corresponding CN Application No. 201580044375.0, dated Dec. 25, 2018.

* cited by examiner

METHODS AND DEVICES FOR IDENTIFYING SUCTION EVENTS

CROSS-REFERENCE TO RELATED APPLICATION

This application is divisional of patent application Ser. No. 14/743,166, filed Jun. 18, 2015, entitled METHODS AND DEVICES FOR INDENTIFYING SUCTION EVENTS and is related to and claims priority to U.S. Provisional Patent Application Ser. No. 62/013,680, filed Jun. 18, 2014, entitled METHODS AND DEVICES FOR INDENTIFYING SUCTION EVENTS, the entirety of which is incorporated herein by reference.

STATEMENT REGARDING FEDERALLY SPONSORED RESEARCH OR DEVELOPMENT n/a

TECHNICAL FIELD

The present invention relates to a method and system for identifying suction events within an implantable blood pump.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as a ventricular assist device or "VAD." Where a VAD is used to assist the pumping action of the left ventricle, the device draws blood from the left ventricle of the heart and discharges the blood into the aorta.

To provide clinically useful assistance to the heart, blood pumps impel blood at a substantial blood flow rate. For an adult human patient, a ventricular assist device may be arranged to pump blood at about 1-10 liters per minute at a differential pressure across the pump of about 10-110 mm Hg, depending on the needs of the patient. The needs of the patient may vary with age, height, and other factors.

It is desirable to monitor the rate at which blood is impelled by a blood pump. For example, if a VAD is operated at a flow rate in excess of the inflow rate of blood to the ventricle, the VAD will create a suction condition within the ventricle, wherein the ventricle is collapsed and essentially devoid of blood. This condition is undesirable. In this condition, the flow rate through the pump will decline rapidly. Likewise, if the intake or outlet of the pump is occluded, the flow rate will decline. If the flow rate through the pump is insufficient, the device will not provide sufficient circulatory assistance to the patient. Excessive flow also can create undesirable conditions. Therefore, it would be desirable to provide a blood pump controller which can monitor the blood flow rate produced by the blood pump which it controls, and determine the presence or absence of a suction condition based on such monitoring.

SUMMARY

One aspect of the present disclosure provides for a method including the steps of: acquiring a plurality of flow rate data points over time, each data point indicative of a flow rate of blood through the pump; calculating, based on the plurality of acquired flow rate data points, a value characterizing one or more features of a waveform formed from the plurality of flow rate data points; and determining, based on the calculated value, the presence or absence of a suction condition in the pump. The calculated value may be calculated based at least in part on one or more parameters derived from the plurality of flow rate data points, such as an average flow rate value, a flow rate waveform amplitude value, or a minimum flow rate value. For example, the waveform index value may be calculated based on a difference between the flow rate waveform amplitude value and minimum flow rate value, divided by the average flow rate value. For further illustration, the value may be indicative of a trough depth, or relative trough depth, of the waveform.

In some examples, the calculated value may be based on a plurality of acquired flow rate values acquired over a duration of one or more cardiac cycles. In this respect, calculating a calculated value may be performed repeatedly over time, and the presence or absence of a suction condition in the blood pump may then be determined based on the plurality of calculated values. In some such examples, each respective calculated value may calculated based on a plurality of acquired flow rate values acquired over a different cardiac cycle. The presence or absence of a suction condition in the pump may be determined based at least in part on a mean, median, mode or standard deviation of the plurality of calculated values.

In some examples, the method may further involve controlling operation of the pump based on the determined presence or absence of a suction condition. Such controlling may include decreasing RPM of a rotor of the pump in response to determining the absence of a suction condition, and/or increasing RPM of a rotor of the pump in response to determining the presence of a suction condition.

Another aspect of the disclosure provides for a control circuit for monitoring operation of an implantable blood pump. The control circuit may include a memory and a processor. The processor may be operative to: determine a plurality of flow rate data points over time, each data point indicative of a flow rate of blood through the pump; calculate, based on the plurality of flow rate data points, a value characterizing one or more features of a waveform formed from the plurality of flow rate data points; and determine the presence or absence of a suction condition at the pump based at least in part on the calculated value. Calculating the calculated value may be based at least in part on parameters derived from the plurality of flow rate data points, such as average, amplitude, maximum or minimum. For example, calculating the value may be based on a difference between the average of the data points and one of a relative maximum and relative minimum of the data points.

The processor may be operative to calculate multiple calculated values, each associated with a different cardiac cycle. Determining the presence or absence of a suction condition at the pump may then be based on the plurality of calculated values, such as using at least one of a mean, median, mode or standard deviation of the values.

Yet another aspect of the disclosure provides for an implantable blood pump system, with a pump including any of the example control circuits provided for herein, a housing having an axis, and further including a rotor disposed within the housing, the rotor being rotatable around the axis. In such a system, the control circuit may be operative to determine the flow rate of blood based on one or a combination of: an acceleration of the rotor; a speed of the rotor; and a back electromotive force induced on the rotor.

The control circuit may be operatively coupled to the pump to control operation of the pump, such as to decrease RPM of the rotor in response to determining the absence of a suction condition, or to increase RPM of the rotor in response to determining the presence of a suction condition.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The present disclosure provides for a blood pump system including a blood pump and a control circuit. The pump is a centrifugal pump, such as the HVAD® Pump manufactured by HeartWare Inc. in Miami Lakes, Fla., USA. The HVAD® Pump is further described in U.S. Pat. No. 8,512,013, the disclosure of which is incorporated by reference herein. In operation, the blood pump draws blood from the left ventricle of a patient's heart and propels the blood through an outflow graft connected to the patient's ascending aorta. Although in the example of the HVAD® Pump, the blood pump is a centrifugal pump, in other examples the blood pump may be an axial flow pump, such as the MVAD® Pump, also manufactured by HeartWare Inc., which is further described in U.S. Patent Publication No. 2012/0245681, the disclosure of which is incorporated by reference herein. In operation, that pump similarly draws blood toward the patient's ascending aorta, but in the same direction from which the blood was drawn from the left ventricle of a patient's heart. In further examples, the blood pump may be any other pump suitable for providing vascular assistance.

Figure 1:
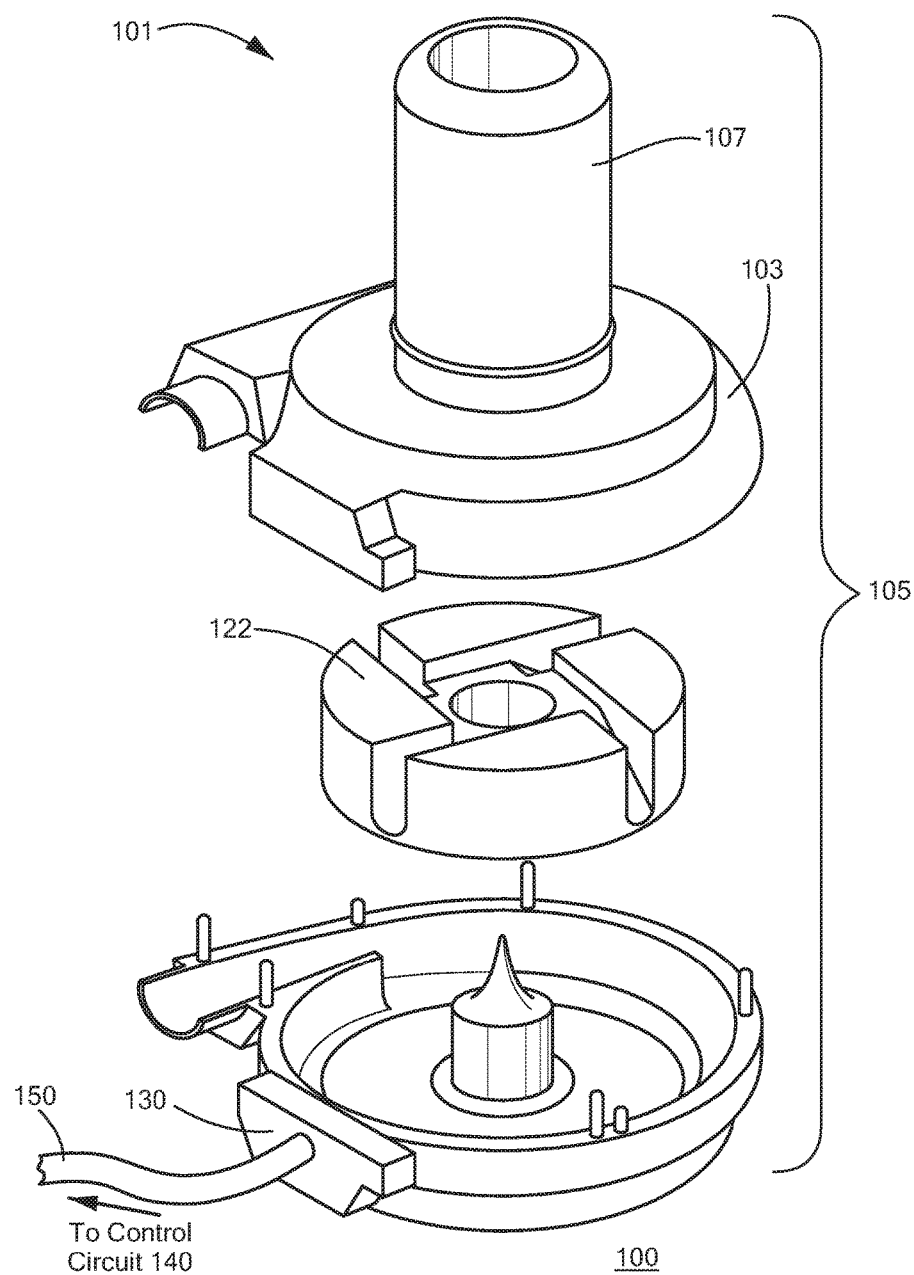
FIG. 1 is an exploded perspective view of a blood pump system in accordance with an aspect of the disclosure.

FIG. 1 depicts a blood pump system 100 in accordance with one embodiment of the invention. The blood pump system 100 according to this embodiment includes a control circuit 140 (not shown) connected via a cable feed 150 to a centrifugal blood pump 101. The blood pump 101 includes a housing 105 consisting of interlocking casings to form a closed pumping chamber 103 between them. Blood is supplied to the pump 101 through an axial inlet cannula 107 adapted for apical insertion into a heart ventricle. The cannula 107 is affixed to or may be integral with the housing 105 and is in fluid flow communication with the pumping chamber 103. Blood exits the pumping chamber 103 through an outlet 113 opposite the inlet cannula 107 in a direction substantially perpendicular to the longitudinal axis of the inlet cannula 107.

A motor rotor or pump impeller 122 is located within the pumping chamber 103. In operation, blood entering the cannula 107 from a heart ventricle passes into the pumping chamber 103 where it is engaged by the rotating impeller 122. Blood entering the pumping chamber from the cannula 107 is redirected from axial flow exiting the cannula to a radial flow within which the impeller 122 is submerged.

The housing 105 may contain an electrical feed through connector 130 for a power and control cable to supply power to the electrical motor of the pump. The cable feed 150 carrying a plurality of cables is connected to the pump through the connector 130. The cables in the feed 150 may carry electrical power and control instructions to the pump 101.

The control circuit 140 monitors and further controls operation of the pump 101. The control circuit functions may be implemented at least in part by a general-purpose processor, as shown in the example implementation of FIG. 2. As shown, the control circuit 140 is implemented using a processor 210, a memory 220, data 230, instructions 240, and an interface 250. Memory 220 stores information accessible by processor 210, including instructions 240 that may be executed by the processor 210. The memory also includes data 230 that may be retrieved, manipulated or stored by the processor 210. The memory may be of any type capable of storing information accessible by the processor, such as a hard-drive, memory card, ROM, RAM, DVD, CD-ROM, write-capable, and read-only memories. The processor 210 may be any well-known processor, such as commercially available processors. Alternatively, the processor may be a dedicated controller such as an ASIC.

Data 230 may be retrieved, stored or modified by processor 210 in accordance with the instructions 240. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data.

The control circuit 140 is coupled to the pump and is operable to collect pump data. The pump data includes speed of rotation of the pump's rotor and amount of current used to drive the pump. In addition, the control circuit is operable to collect flow rate data points 232 indicative of a flow rate of blood exiting the pump when the pump is used to propel blood from the heart's left ventricle into the aorta. The data points may be acquired using a model for the estimation of blood flow rate. In one example, the model determines blood flow rate based in part on the acceleration of the rotor of the pump and possibly the viscosity of the patient's blood (e.g., based on hematocrit levels). Using such a model results in the estimate having a dynamic range of about 15 Hz.

In other examples, other parameters indicative of flow may be used, and/or different calculations may be employed, to estimate a flow rate of blood. Alternatively, flow rate data points may be gathered using direct measurements, such as with an ultrasonic flow meter.

In addition to the flow rate data points 232, the data 230 may further include flow rate parameters, or values, 234 calculated based on several collected data points over time. The flow rate parameters 234 may include an average flow rate value, a maximum flow rate value, a minimum flow rate value, and a flow rate waveform amplitude value. Each of these values may be repeatedly updated. For instance, the average flow rate value may be a moving average. Similarly, the maximum, minimum (or flow trough), and amplitude (or flow pulsatility) values may be collected for every cardiac cycle (or a predetermined number of cardiac cycles) of the patient. Additionally, and as explained in greater detail below, the data 230 may further include waveform index values (or indices) 236 calculated based on the parameters 234 of the flow rate waveform. The waveform index values 236 of the flow rate waveform may be used to determine the presence or absence of a suction condition at the pump 101.

In alternative embodiments, the data 230 may include further information to estimate blood flow through the pump. For example, the data 230 in a control circuit operatively coupled to an axial flow pump may include one or more current-to-flow table to estimate the blood flow rate based on a measured electrical current used to drive the pump. As explained in greater detail in commonly owned U.S. Patent Publication No. 2012/0245681, the disclosure of which is hereby incorporated herein by reference, such estimates may be determined based further on the given rotor speed of the pump, a back electromotive force induced by the impeller on the coils of the rotor, and possibly the viscosity of the patient's blood.

The instructions 240 stored in the memory may include one or more instruction sets or modules for performing certain operations in accordance with the present disclosure. One such module may be a flow estimation module 242 for performing the steps required to estimate a flow rate of blood through the pump. Another such module may be a pump control module 244 for controlling operation of the pump 101, such as in response to determining the presence, absence, or clearance of a suction condition at the pump.

The control circuit 140 may optionally include an interface 250 which connects the control circuit 140 to an output device 260. The interface 250 may be an analog interface (e.g., audio interface) or a digital interface, such as Bluetooth, TCP/IP, wi-fi, and others. Where the control circuit is implemented in an implantable structure adapted to be disposed within the body of the patient, the interface 250 may include known elements for communicating signals through the skin of the patient. The output device 260, may be a speaker, a light, a communications terminal (e.g., computer, cell phone), or any other type of device.

Figure 2:
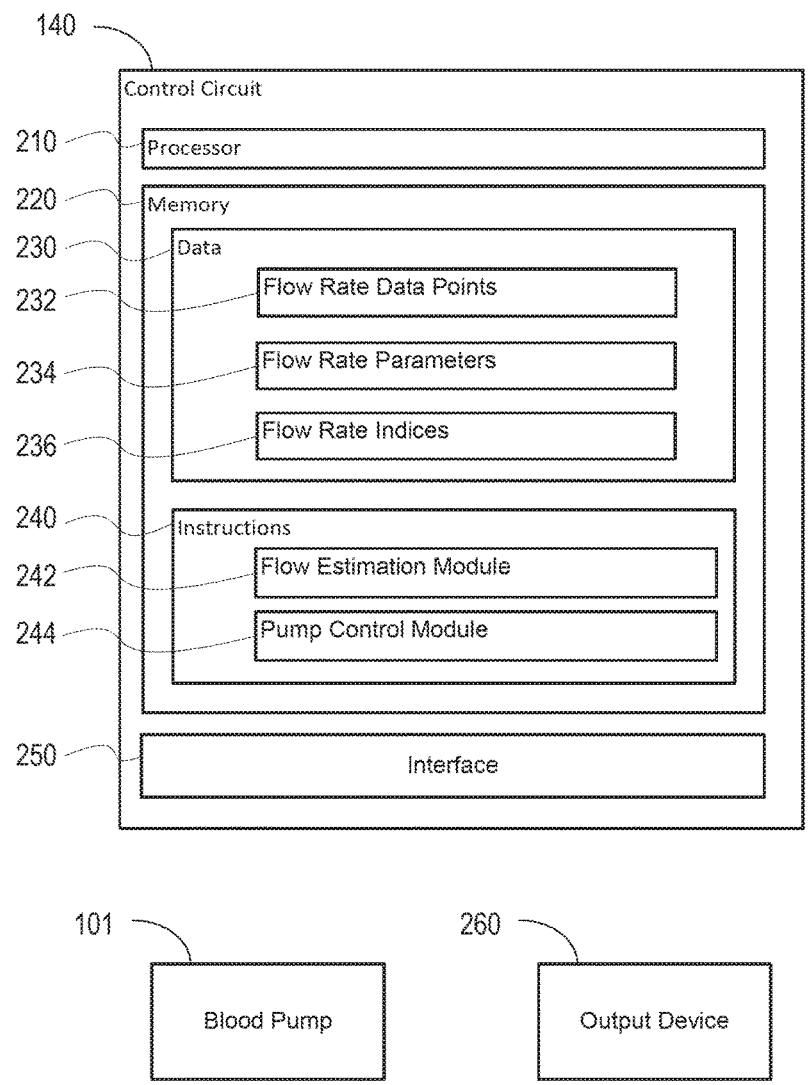
FIG. 2 is a block diagram of the control circuit of the blood pump system of FIG. 1.

Although FIG. 2 functionally illustrates the processor and memory as being within the same block, it will be understood that the processor and memory may actually comprise multiple processors and memories that may or may not be stored within the same physical housing. The memory may include one or more media on which information can be stored. Preferably, the medium holding the instructions retains the instructions in non-transitory form. Some or all of the instructions and data may be stored in a location physically remote from, yet still accessible by, the processor. Similarly, the processor may actually comprise a collection of processors which may or may not operate in parallel.

The example systems described above may be operated using the methods described herein. It should be understood that the following operations do not have to be performed in the precise order described below. Rather, various operations can be handled in a different order or simultaneously. It should also be understood that these operations do not have to be performed all at once. For instance, some operations may be performed separately from other operations. Moreover, operations may be added or omitted.

Figure 3:
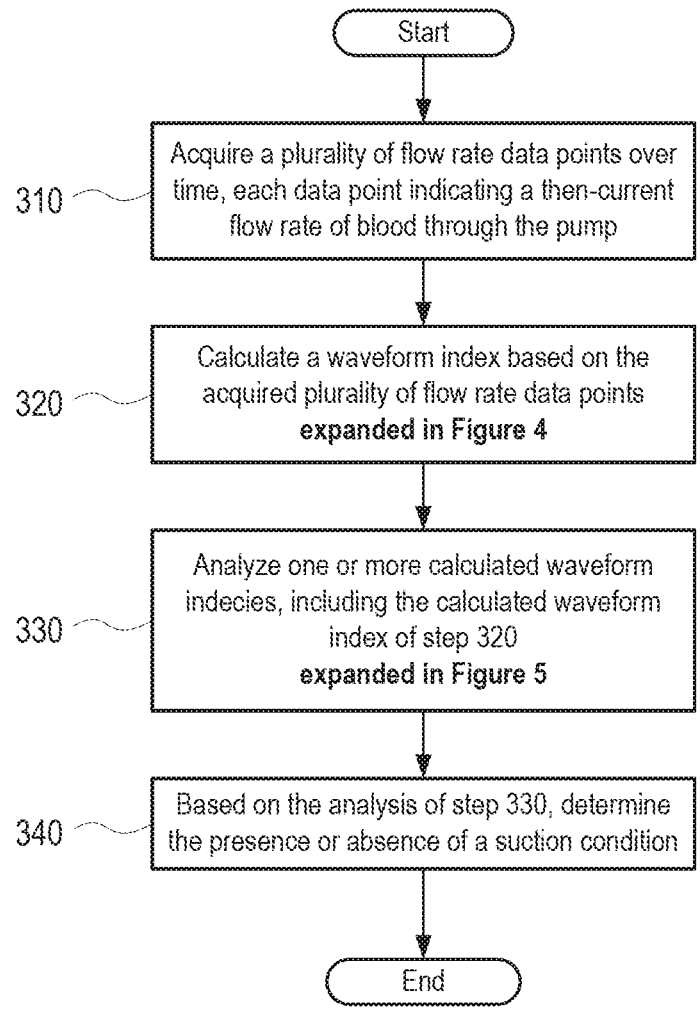
FIGS. 3, 4 and 5 are flow diagrams of methods for monitoring operation of a blood pump in accordance with an aspect of the disclosure.

FIG. 3 is a flow diagram depicting operations 300 of the control circuit 140 in conjunction with the above described objectives. At task 310, the control circuit acquires a plurality of flow rate data points over time. The flow rate data points may be acquired using the flow rate estimation or measurement techniques described above, with each flow rate data point indicating a then-current flow rate of blood through the pump 101 at the time of the flow rate estimation or measurement. Collectively, the plurality of data points make up a flow waveform, showing the changes in flow through the pump over the course of one or more cardiac cycles.

At task 320, the control circuit calculates a waveform index based on the acquired plurality of flow rate data points from task 310. The waveform index is a calculated value that characterizes one or more features of the waveform of flow rate data points. In one example of the present disclosure (described in greater detail in FIGS. 6-8), the waveform index indicates a relative depth of a trough or minimum of the waveform, as compared to the other data points of the waveform, or as compared to other the local minima of the waveform if the waveform includes data points taken over the span of multiple cardiac cycles. More generally, the waveform index may be based on a difference between the average of the acquired data points and a relative minimum of the data points, thereby indicating an excessive deviation in flow.

In order to calculate the waveform index, several other features of the waveform, such as a mean and/or median flow rate, may also be determined from the plurality of data points. Additionally, for a given cardiac cycle, a maximum, minimum, and amplitude may be determined.

Figure 4:
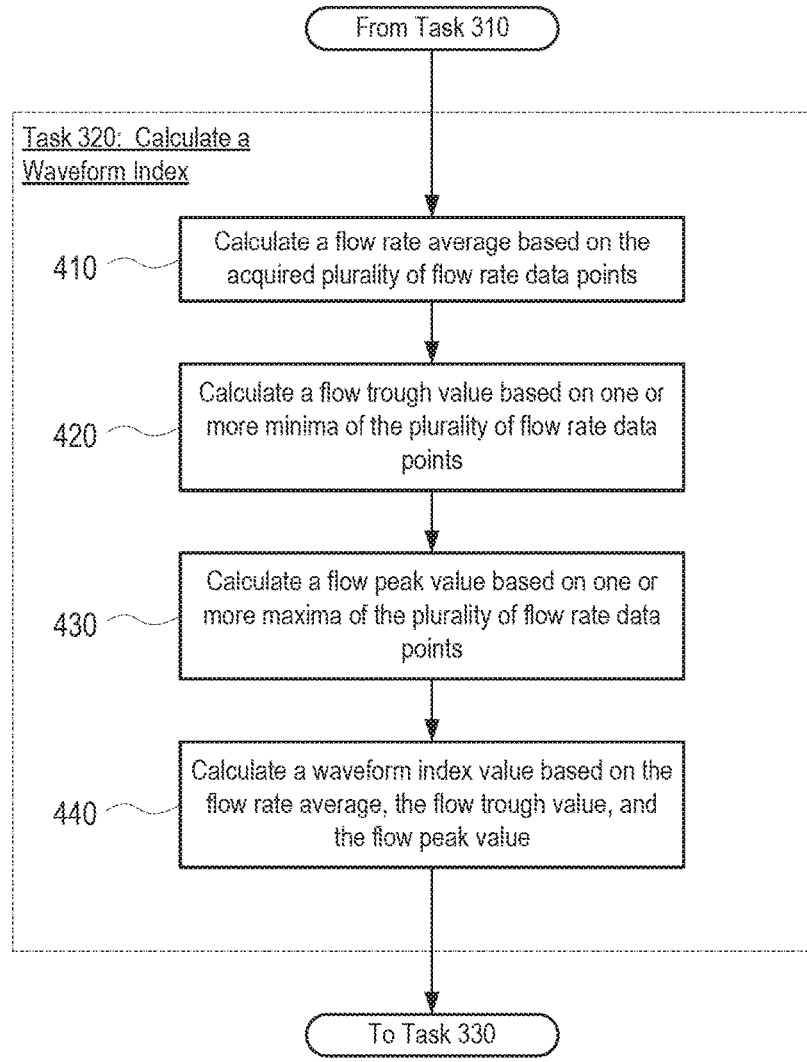

FIG. 4 is a flow diagram depicting an example set of operations 400 by the control circuit 140 to calculate a waveform index for a given cardiac cycle, in accordance with task 320. At task 410, the control circuit calculates an average flow rate based on the acquired plurality of flow rate data points. The average may be calculated based only on the flow rate data points associated with the given cardiac cycle. Alternatively, the average may be a repeatedly updated moving average, such that the calculation is further based on flow rate data points from previous cardiac cycles. For instance, a moving average may be calculated based on flow rate data points over a span of several cardiac cycles, several hours (e.g., three hours), several days (e.g., three days) or even longer. In the examples of the present disclosure, the average is a moving average with a k-value of about 0.01 to about 0.02 (about 50 to about 100 data points).

At task 420, the control circuit calculates a flow trough value. The flow trough value may correspond to a minimum flow rate during the given cardiac cycle. Alternatively, the flow trough value may be based on two or more local minima of flow rate data points from previous cardiac cycles, such as by calculating an average or median of the local minima.

At task 430, the control circuit calculates a flow peak value. Much like the flow trough value, the flow peak value may correspond to a maximum flow rate during the given cardiac cycle. Alternatively, the flow peak value may be based on (such as an average or median) two or more local maxima of flow rate data points from previous cardiac cycles. The flow peak and flow trough values may further yield a flow pulsatility value, which is the difference between the peak and trough values. Where the peak and trough values are associated with a given cardiac cycle, the flow pulsatility value is effectively an amplitude of the flow waveform over the cardiac cycle.

At task 440, the control circuit calculates the waveform index based on the flow rate average, flow trough value, and flow peak value determined in the previous tasks. This determination may be performed using the following formula:

$$\text{Flow Index} = \frac{\text{Average Flow} - \text{Flow Trough}}{\text{Flow Pulsatility}} \qquad (1)$$

In the above formula, the waveform index is a value characterized based on a ratio between (i) the overall amplitude of the waveform, and (ii) the difference between the minimum of the waveform and the average flow rate. Generally, and as shown below in FIGS. 7A and 7B of the disclosure, the waveform index calculated during normal operation of the pump will be lower than the waveform index calculated during a suction event. Thus, the waveform index can be used to identify the absence or presence of a suction condition based on the waveform of flow rate data points over the course of one or more cardiac cycles.

The control circuit may perform task 320 once or repeatedly in the process of the determining the presence or absence of a suction condition. Returning to FIG. 3, at task 330, the control circuit analyzes the one or more flow rate indices calculated at task 320. In those cases where a single waveform index value has been calculated, the analysis performed at task 330 may involve comparing that index value to a threshold value, and then determining, at task 340, whether the index value is or is not indicative of a suction condition based on the comparison. For instance, a waveform index exceeding the threshold value can indicate the presence of a suction condition, whereas a waveform index not exceeding the threshold can indicate the absence of a suction condition.

In some circumstances, a single waveform index value taken over the course of a single cardiac cycle may not provide enough information to definitively identify the presence or absence of a suction conduction. For instance, the range of waveform index values yielded during a suction event may overlap with the range of waveform index values yielded during normal operation of the pump. Therefore, it may be further beneficial to collect multiple flow rate indices over the course of multiple cardiac cycles, and to determine the presence or absence of a suction condition based on the multiple flow rate indices.

Figure 5:
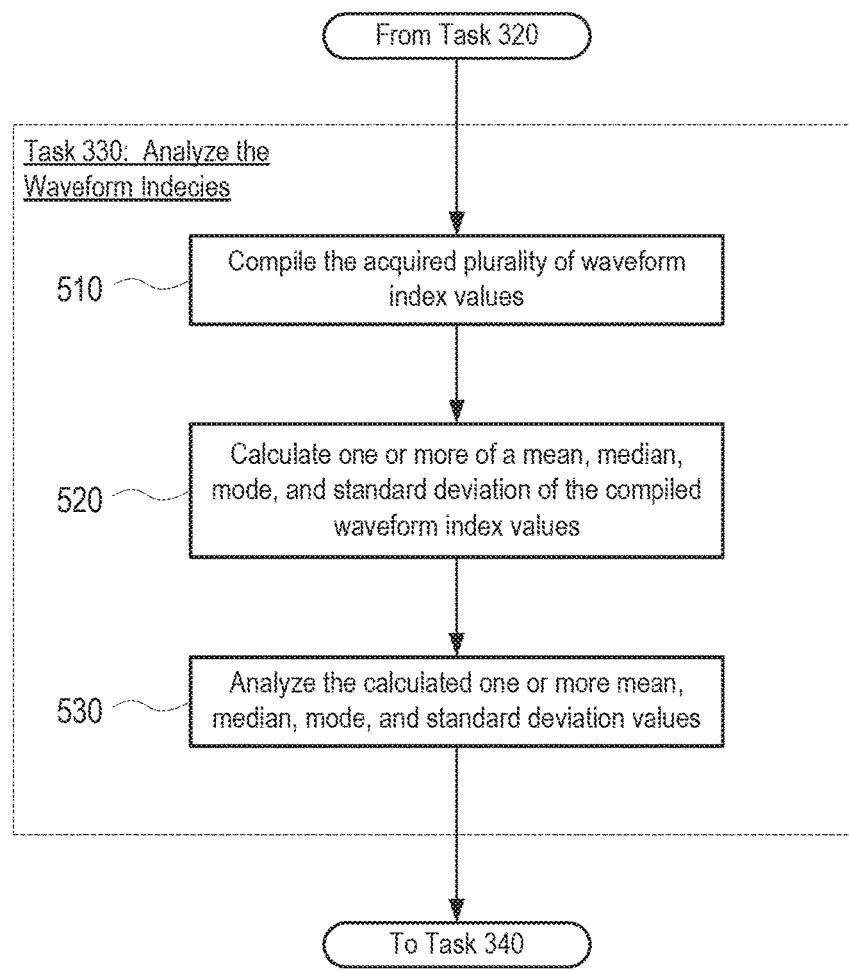

FIG. 5 is a flow diagram depicting operations 500 of the control circuit 140 in conjunction with this objective, in which multiple flow rate indices are analyzed at task 330. At task 510, the control circuit compiles the multiple flow rate indices calculated during the repeated performance of task 320. At task 520, features of the compiled waveform index data are then calculated. For example, an average, median, or mode waveform index value may be calculated from the compiled indices. Additionally, a standard deviation of the compiled values may be determined.

Figure 8:
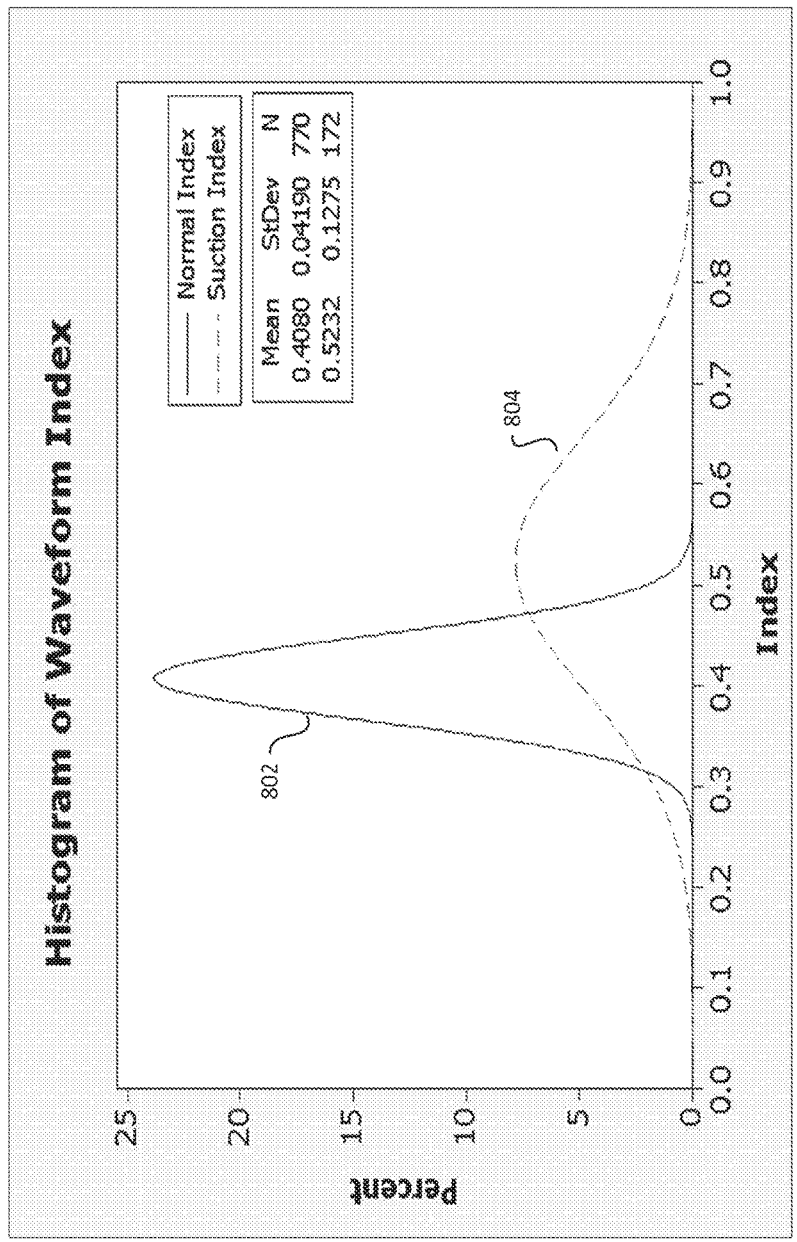
FIG. 8 is a histogram of calculated waveform indices in accordance with an aspect of the disclosure.

At task 530, one or more of the calculated mean, median, mode, and/or standard deviation features may be compared to corresponding threshold values. With regard to the calculated mean, median and mode waveform index and corresponding threshold values, comparing these values is similar to the analysis of a single waveform index, in which exceeding the threshold may indicate the presence of a suction condition, whereas not exceeding the threshold can indicate the absence of a suction condition. With regard to the calculated standard deviation and corresponding threshold, generally, and as shown in FIG. 8 of the disclosure, the flow rate indices calculated during normal operation of the pump will be subject to less variation than the flow rate indices calculated during a suction event. Thus, exceeding a threshold standard deviation may indicate the presence of a suction condition, whereas not exceeding the threshold standard deviation can indicate the absence of a suction condition The above examples rely on a comparison to a threshold value. However, in other examples, the one or more calculated flow rate indices may be analyzed differently. For instance, the flow rate indices may be classified using a statistical model (e.g., Bayes analysis) or a neural network.

Figure 6A:
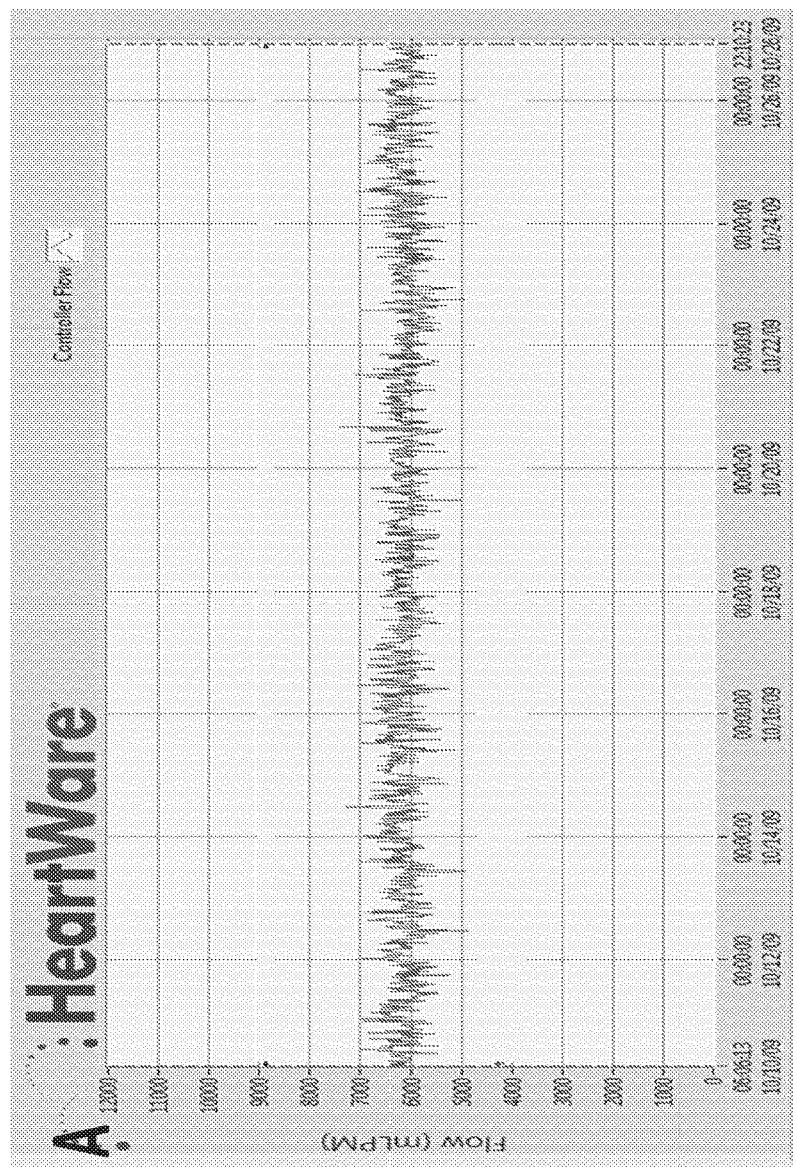
FIGS. 6A and 6B are graphical representations of flow rate in a blood pump over time in accordance with an aspect of the disclosure.
Figure 6B:
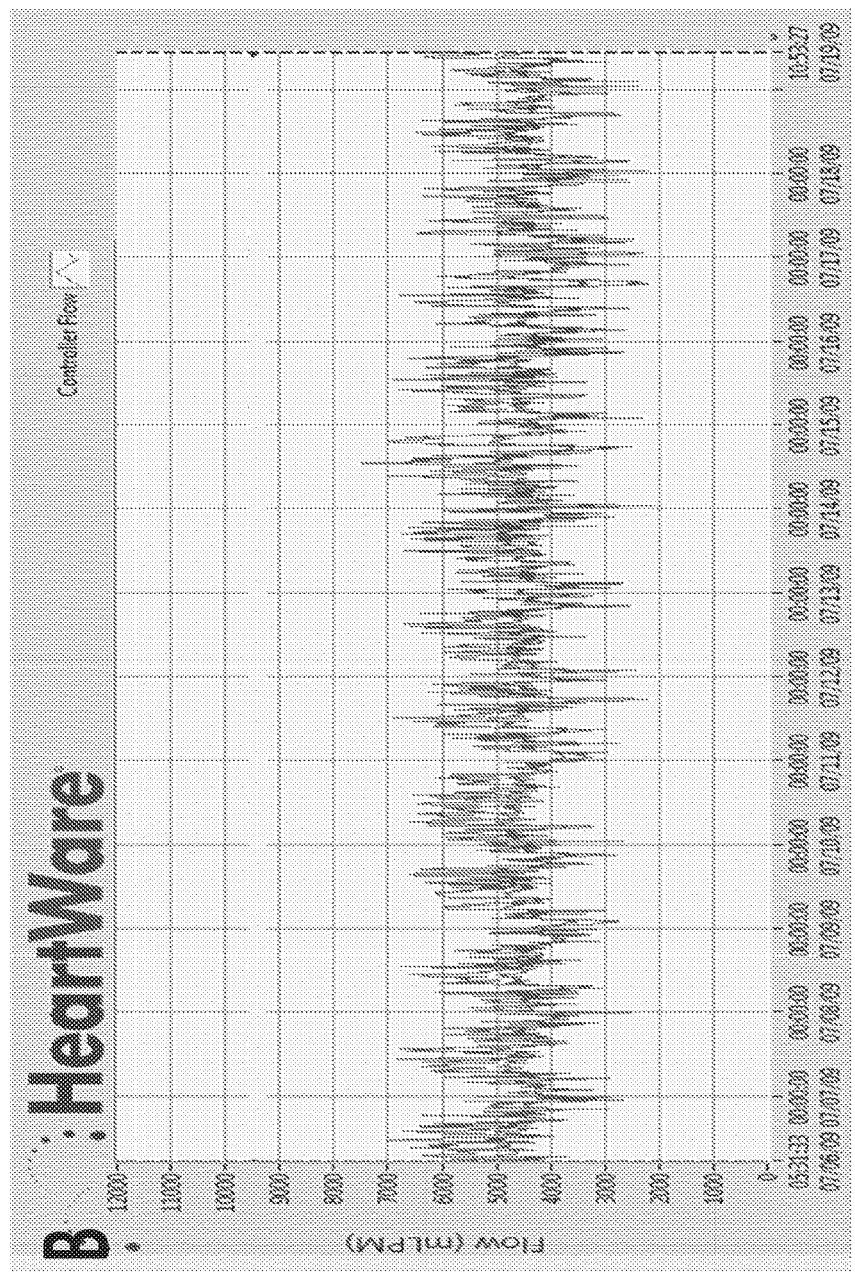

FIGS. 6A-6B, 7A-7B and 8 are provided herein to illustrate an example of the above methods. FIGS. 6A and 6B are graphical representations of estimated flow values in a blood pump logged over time, in this case over the course of several days. Specifically, the estimated flow values shown in FIG. 6A make up a waveform that is representative of flow under normal operating conditions of the blood pump. By contrast, the estimated flow values shown in FIG. 6B make up a waveform that is representative of flow under suction conditions (during a suction event). As seen from FIGS. 6A and 6B, the waveform associated with normal conditions is relatively more stable than that associated with a suction condition. More specifically, the waveform associated with normal conditions does not include any intermittent decreases in average flow (e.g., averaged over the span of one day) that are greater than 1 L/min, whereas the waveform associated with a suction condition includes such intermittent decreases.

Figure 7A:
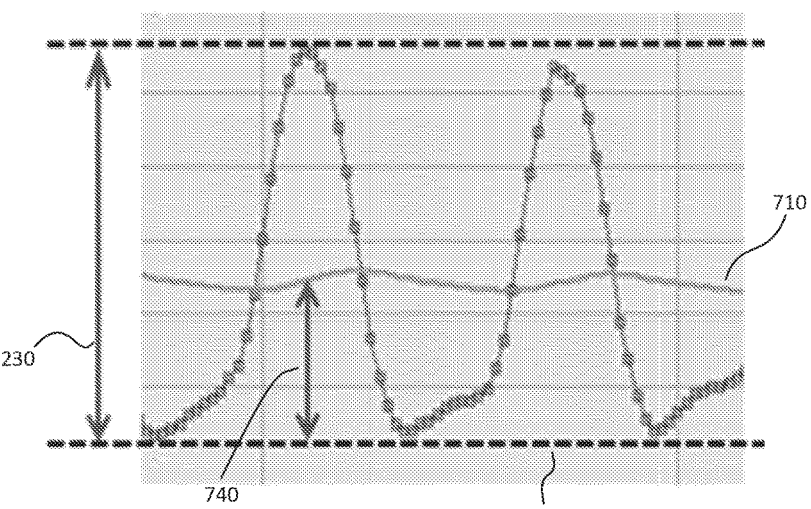
FIGS. 7A and 7B are graphical representations of parameters used in calculating a waveform index value based on flow rate in a blood pump over time in accordance with an aspect of the disclosure.
Figure 7B:
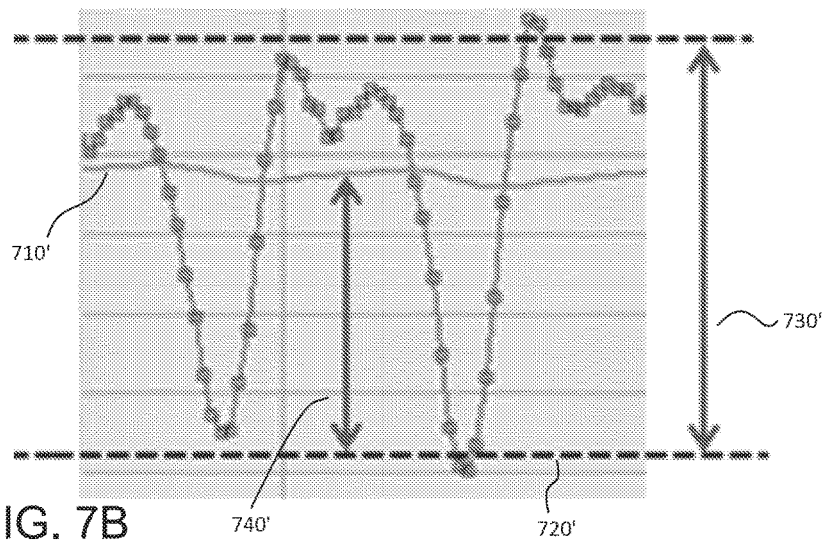

FIGS. 7A and 7B are close-up illustrations of portions of the flow rate waveforms shown in FIGS. 1A and 1B, respectively. The dots depicted along each waveform are flow rate data points representative of logged estimated flow values. Also shown in FIGS. 7A and 7B are additional waveform features or parameters used in charactering the flow rate waveform, such as flow average, flow pulsatility, and flow trough. The waveforms in FIGS. 7A and 7B are not necessarily drawn to scale with one another.

In the examples of FIGS. 7A and 7B, the waveform index is calculated for a given cardiac cycle. Given a plurality of logged estimated flow values over the cardiac cycle, the control circuit may calculate a flow average 710, 710' based on the moving average value of the estimated flow values, a flow trough 720, 720' based on the minimum logged flow value during the cardiac cycle, and the flow pulsatility 730, 730' based on the difference between the maximum logged flow value and the minimum logged flow value during the cardiac cycle. In the present example, the minimum logged value is an absolute minimum value. In other examples, a mean value of local minima, or a median value of local minima, may be used. Similar values may be used for the maximum logged flow value in calculating flow pulsatility.

With attention to FIG. 7B, the suction condition is shown to cause sudden and sharp decreases in flow. In turn, the flow trough of FIG. 7B is relatively lower than that in FIG. 7A. Therefore, the flow pulsatility in FIG. 7B is relatively greater than that in FIG. 7A. As a result, while the average flow during a suction event (FIG. 7B) is generally lower than during normal operation (FIG. 7A), the difference between average flow and flow trough during a suction event can actually be much larger than during normal operation.

The control circuit further calculates a waveform index based on the above formula (1). In the example of FIG. 7A, the difference between the calculated average flow and flow trough 240 is about 40% of the flow pulsatility 230. Therefore, the calculated waveform index is about 0.4. For further example, in FIG. 7B, the difference between the calculated average flow and flow trough 240' is about 65% of the flow pulsatility 230'. Therefore, the calculated waveform index is about 0.65.

As the control circuit calculates flow rate indices based on the logged flow estimation data, the control circuit further compiles the calculated values of indices. FIG. 8 illustrates two such compilations of waveform index values in the form of two overlaid histograms having normalized distribution curves. The left histogram 802 of FIG. 8 is representative of compiled waveform index values under normal operating conditions of the blood pump, and the right histogram 804 is representative of compiled waveform index values during a suction event. As depicted in FIG. 8, normal operating conditions yield a distribution curve of flow rate indices having an overall lower average index value, and having a lower standard deviation (a greater density) as compared to the distribution curve of index values compiled during suction conditions. Specifically, the average and standard deviation of the left histogram 802 is 0.41±0.04, as compared to the right histogram 804, which is 0.52±0.13 ($p<0.001$).

As seen from the above calculations, the flow rate data logged by the control circuit may be used to determine the presence or absence of a suction condition. Such determination may be performed by calculating waveform index values and further analyzing those calculated values. Such analysis may involve calculating a mean or median waveform index value, in which case a relatively low index value (e.g., 0.4) may be indicative of normal operating conditions, whereas a relatively high index value (e.g., 0.65) may be indicative of a suction condition. Furthermore, analysis of waveform index values may involve calculating a standard deviation value, in which case a relatively low standard deviation value (e.g., ±0.04) may be indicative of normal operating conditions, whereas a relatively high standard deviation value (e.g., ±0.13) may be indicative of a suction condition.

In the above example, the logged flow rate data may be stored in the blood pump memory and processed by a device external to the blood pump. For instance, the logged data may be downloaded from the control circuit and processed on another computer in order to analyze recent operation of the blood pump. Alternatively, or additionally, the control circuit itself may include circuitry capable of analyzing the logged data. In such a scenario, the control circuit may be capable of itself determining the presence or absence of a suction condition based on the logged data, and may control operation of the blood pump based on such a determination. For instance, in the presence of a suction condition, the control circuit may control a slowing in the speed of the blood pump (e.g., reducing the RPM of a rotor in the blood pump) until the suction condition is determined to have cleared. Clearance of the suction condition may similarly based on an analysis of the logged flow rate data in the manner described above.

While the above disclosure provides examples of calculating a waveform index and identifying suction conditions, based on flow data, it is also possible to perform similar calculations and determinations based on other data. For instance, data relating to an amount of electrical current provided to the blood pump may similarly be acquired repeatedly and used to acquire a sequence or waveform of data points, and thereby used to calculate a waveform index and identify whether a suction condition is present. Any other parameter related to or indicative of flow in the blood pump may similarly be utilized. If a parameter that is inversely related to the flow rate of blood were to be used, then the waveform index value may be indicative of a relative maximum in the waveform (such as the difference between the average of the waveform and the relative maximum), as opposed to a relative trough or minimum in the waveform (as in the example of FIGS. 6-8).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A control circuit for monitoring operation of an implantable blood pump, the control circuit comprising:
   a memory; and
   a processor configured to:
   determine a plurality of flow rate data points over time, each of the plurality of flow rate data points indicative of a flow rate of blood through an implantable blood pump;
   determine a flow rate waveform amplitude value based on the plurality of flow rate data points over time;
   calculate, based on the plurality of flow rate data points and the flow rate waveform amplitude value, a value characterizing a plurality of features of a waveform formed from the plurality of flow rate data points, the plurality of features including a relative trough depth of the waveform, the relative trough depth of the waveform being based on at least two local minima of the plurality of flow rate data points from previous cardiac cycles;
   determine one of a group consisting of a presence and an absence of a suction condition at the pump based at least in part on the value; and
   control a speed of the implantable blood pump based on the determined at least one of the presence and the absence of the suction condition.

2. The control circuit of claim 1, wherein the processor is configured to calculate the value based on a difference between an average of the plurality of flow rate data points and one of a group consisting of a relative maximum and a relative minimum of the plurality of flow rate data points.

3. The control circuit of claim 1, wherein the processor is configured to calculate the value based at least in part on at least one parameter derived from the plurality of flow rate data points, the at least one parameter including at least one of a group consisting of an average flow rate value, the flow rate waveform amplitude value, and a minimum flow rate value.

4. The control circuit of claim 1, wherein the processor is configured to calculate a plurality of values, each of the plurality of values associated with a different cardiac cycle, and determine the one of the group consisting of the presence and the absence of the suction condition at the pump based on the plurality of values.

5. The control circuit of claim 4, wherein the processor is configured to determine the one of the group consisting of the presence and the absence of the suction condition at the pump based on at least one of a mean, a median, a mode, and a standard deviation of the plurality of values.

6. An implantable blood pump system, comprising:

a pump including a housing having an axis and a rotor disposed within the housing, the rotor being rotatable around the axis; and a control circuit including:

a memory; and a processor configured to:

determine a plurality of flow rate data points over time, each data point indicative of a flow rate of blood through the pump;

determine a flow rate waveform amplitude value based on the plurality of flow rate data points over time;

calculate, based on the plurality of flow rate data points and the flow rate waveform amplitude value, a value characterizing a plurality of features of a waveform formed from the plurality of flow rate data points, the plurality of features including a relative trough depth of the waveform, the relative trough depth of the waveform being based on at least two local minima of the plurality of flow rate data points from previous cardiac cycles;

determine one of a group consisting of a presence and an absence of a suction condition at the pump based at least in part on the value; and control a speed of the pump based on the determined at least one of the presence and the absence of the suction condition.

7. The implantable blood pump system of claim 6, wherein the control circuit is configured to determine the flow rate of blood based at least in part on an acceleration of the rotor.

8. The implantable blood pump system of claim 6, wherein the control circuit is configured to determine the flow rate of blood based at least in part on the speed of the rotor and a back electromotive force induced on the rotor.

9. The implantable blood pump system of claim 6, wherein the control circuit is coupled to the pump to control operation of the pump based on the one of the group consisting of the presence and the absence of the suction condition.

10. The implantable blood pump system of claim 9, wherein the control circuit is coupled to the pump to decrease RPM of the rotor in response to determining the absence of the suction condition.

11. The implantable blood pump system of claim 9, wherein the control circuit is coupled to the pump to increase RPM of the rotor in response to determining the presence of the suction condition.

* * * * *